US009545481B1

(12) United States Patent
Rafaat

(10) Patent No.: US 9,545,481 B1
(45) Date of Patent: *Jan. 17, 2017

(54) PRE-LOADED SYRINGE WITH METERED DOSING AND METHODS OF USE

(71) Applicant: Karim Timothy Rafaat, La Jolla, CA (US)

(72) Inventor: Karim Timothy Rafaat, La Jolla, CA (US)

(*) Notice: Subject to any disclaimer, the term of this patent is extended or adjusted under 35 U.S.C. 154(b) by 351 days.

This patent is subject to a terminal disclaimer.

(21) Appl. No.: 14/213,101

(22) Filed: Mar. 14, 2014

Related U.S. Application Data

(63) Continuation-in-part of application No. 13/874,256, filed on Apr. 30, 2013, now Pat. No. 9,302,052.

(51) Int. Cl.
*A61M 5/315* (2006.01)
*A61M 5/31* (2006.01)

(52) U.S. Cl.
CPC .. *A61M 5/31536* (2013.01); *A61M 2005/3126* (2013.01); *A61M 2005/3154* (2013.01)

(58) Field of Classification Search
CPC ............ A61M 5/3155; A61M 5/31536; A61M 2005/3124; A61M 2005/3154
See application file for complete search history.

(56) References Cited

U.S. PATENT DOCUMENTS

| | | | | |
|---|---|---|---|---|
| 5,352,208 A | * | 10/1994 | Robinson | A61M 5/3243 604/111 |
| 7,470,259 B2 | * | 12/2008 | Hoyle, Jr. | A61M 5/2429 604/186 |
| 9,302,052 B1 | * | 4/2016 | Rafaat | A61M 5/31578 |
| 2003/0075168 A2 | * | 4/2003 | Alchas | A61M 15/08 128/200.14 |
| 2004/0162528 A1 | * | 8/2004 | Horvath | A61M 5/31548 604/207 |
| 2006/0173408 A1 | * | 8/2006 | Wyrick | A61M 5/2033 604/110 |
| 2008/0108952 A1 | * | 5/2008 | Horvath | A61M 5/31548 604/208 |
| 2014/0303565 A1 | * | 10/2014 | Kubo | A61M 15/08 604/208 |

* cited by examiner

*Primary Examiner* — Aarti B Berdichevsky
(74) *Attorney, Agent, or Firm* — Sheppard Mullin Richter & Hampton LLP

(57) ABSTRACT

Methods and devices for metering and delivering a desired dose of medication from a syringe are described. The devices may include a dosage limiting sleeve adjustably disposed around a syringe body, wherein the alignment of the dosage limiting sleeve relative to the syringe body indicates the dose to be administered by depressing a plunger until the dosage limiting sleeve is engaged.

8 Claims, 11 Drawing Sheets

PRE-LOADED SYRINGE WITH METERED DOSING AND METHODS OF USE

CROSS-REFERENCE TO RELATED APPLICATIONS

This application is a continuation-in-part of and claims the benefit of U.S. patent application Ser. No. 13/874,256 filed Apr. 30, 2013, which is incorporated herein by reference in its entirety.

TECHNICAL FIELD

The present disclosure is generally related to liquid medication delivery devices and their methods of use. In particular, the present disclosure provides a syringe body with an adjustable plunger stop to meter a single dose to be delivered.

BACKGROUND

In a hurried and pressure-ridden work environment, such as a surgical operating room, there is always a risk for errors to occur. Medication errors may be particularly at risk in the event of an emergency administration of an injectable drug, e.g., while a patient is coding. This is because performing the appropriate calculations to account for drug concentration and volume to be administered based on patient physical characteristics can be difficult under heightened stress conditions. In fact, the steps involved in drug dose calculation, preparation, and administration are constantly identified as steps in pediatric resuscitation that are prone to error, and may be associated with significant morbidity and/or mortality in emergency situations.

Moreover, medication errors related to emergency administration of an injectable medication are not limited to surgical operating rooms. Health care arenas where emergency administrations (to adults, children, or both) occur infrequently are typically staffed by personnel who are less than ideally familiar with calculation, preparation, and administration of injectable medications under emergency conditions.

SUMMARY

In accordance with one embodiment, a syringe comprises a syringe body for storing and dispensing a substance contained within the syringe body. The syringe further comprises a plunger arranged partially within the syringe body such that translational motion of the plunger in a proximal direction causes the substance to be dispensed from the syringe body. Further still, the syringe comprises a dosage limiting sleeve adjustably disposed about the syringe body and extending in a distal direction beyond a distal end of the syringe body, wherein a distal end of the dosage limiting sleeve is configured to interact with the plunger so as to prevent the translational motion of the plunger in the proximal direction beyond a predetermined point, and wherein the dosage limiting sleeve does not limit translational motion of the plunger in a distal direction.

In accordance with another embodiment, a method of administering a liquid medication to a patient with a pre-loaded syringe comprises adjusting at least one of a syringe body and a dosage limiting sleeve relative to the other of the at least one of the syringe body and the dosage limiting sleeve. The syringe body is configured for storing and dispensing the liquid medication contained within the syringe body, and the dosage limiting sleeve is disposed about the syringe body and extending in a distal direction beyond a distal end of the syringe body. A distal end of the dosage limiting sleeve is configured to interact with a plunger so as to prevent translational motion of the plunger in a proximal direction beyond a predetermined point, the plunger arranged partially within the syringe body such that the translational motion of the plunger in the proximal direction causes the liquid medication to be dispensed from the syringe body. The method further comprises moving the plunger in the proximal direction within the syringe body until a proximal end of the plunger aligns with a desired non-volumetric graduation disposed on the syringe body.

In accordance with still another embodiment, a non-volumetric graduated device comprises a syringe body and an adhesive material that is attachable to the syringe body. The adhesive material comprises non-volumetric graduations displayed thereon for indicating an appropriate dose of a liquid medication by patient weight to be dispensed from the syringe body.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1:
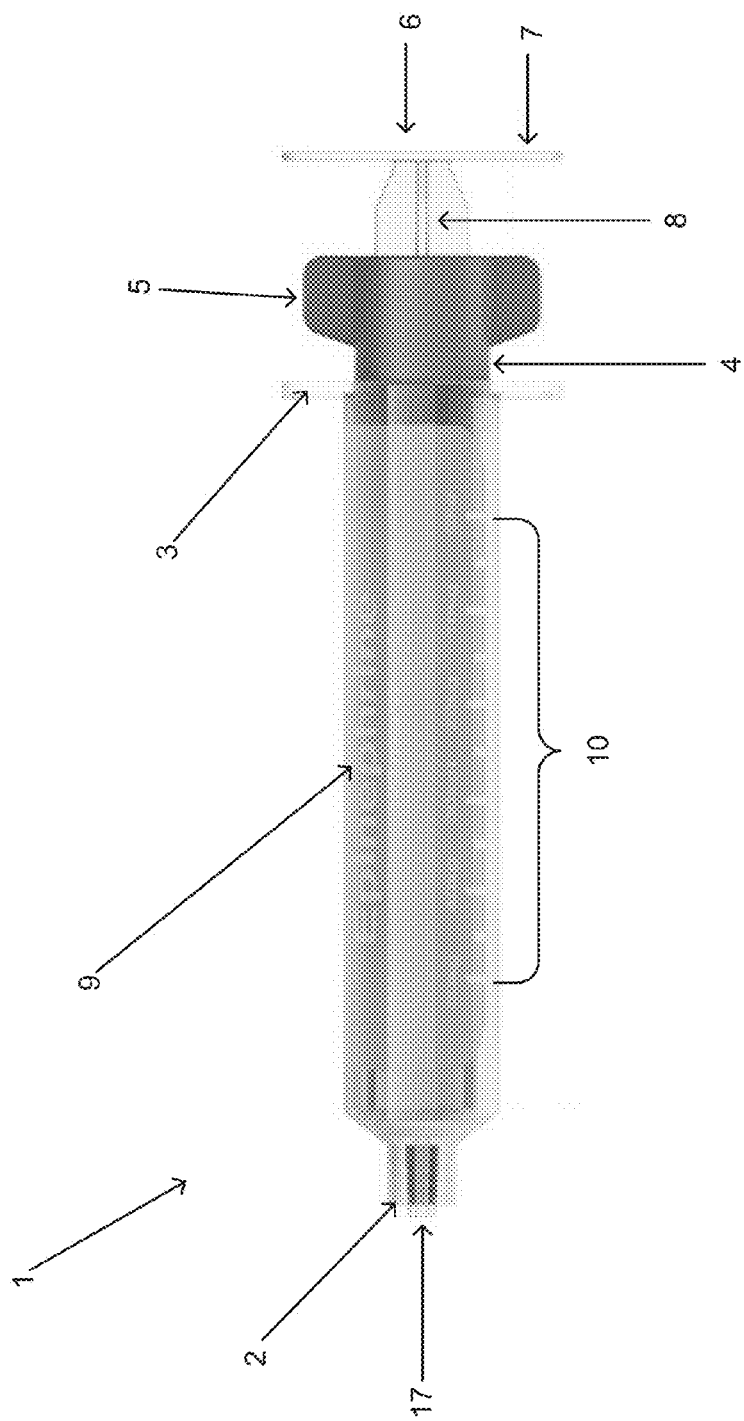
FIG. 1 is a side view of an example syringe according to one embodiment.
Figure 2:
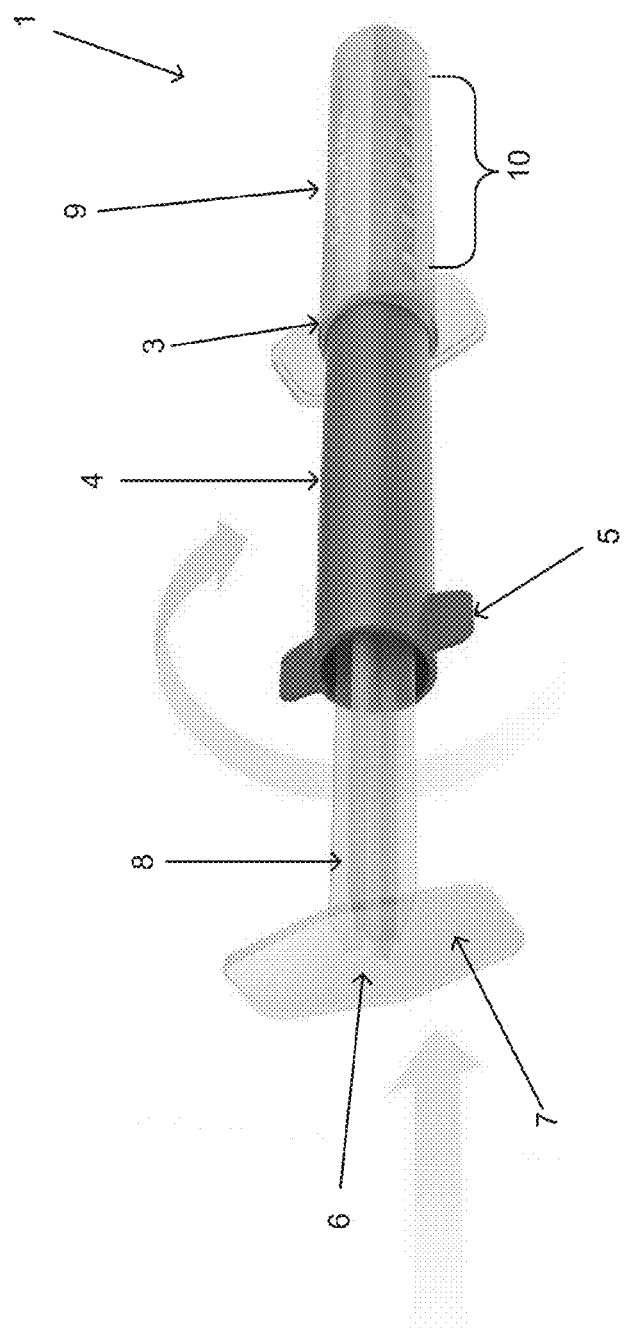
FIG. 2 is an off-axis view from the distal end of an example syringe according to one embodiment.
Figure 3:
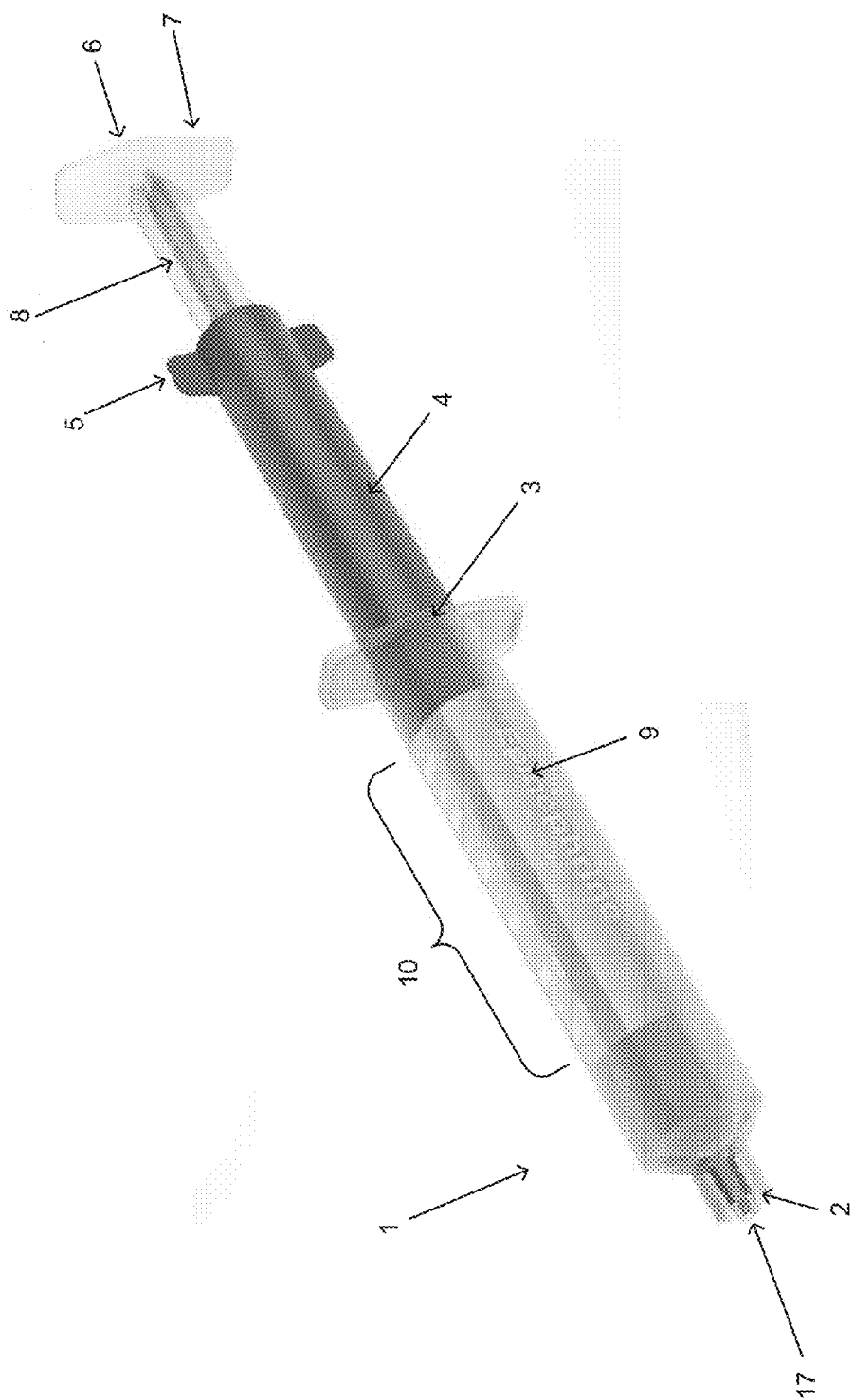
FIG. 3 is an off-axis view from the proximal end of an example syringe according to one embodiment.
Figure 4:
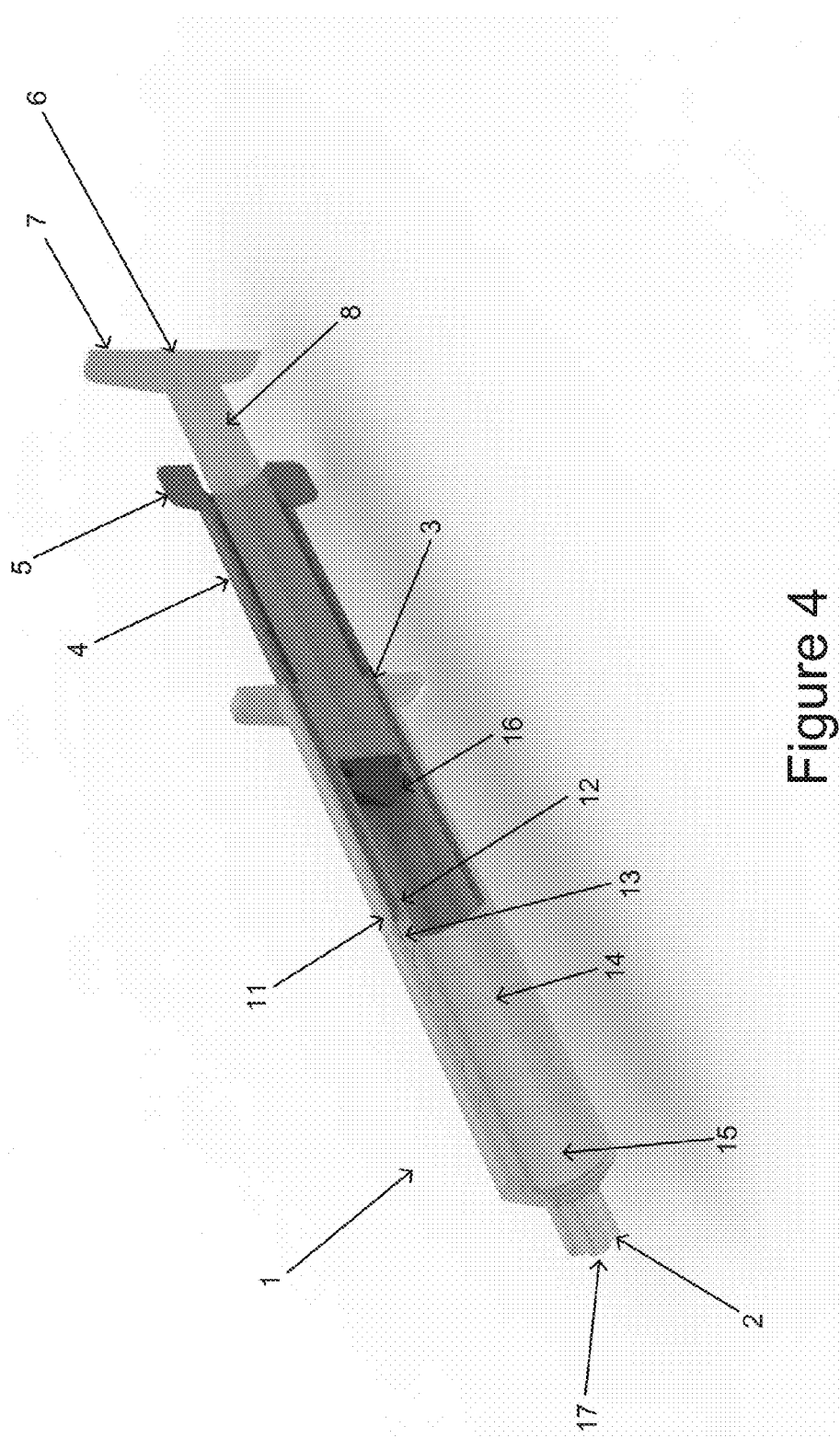
FIG. 4 is a cross-sectional view of an example syringe according to one embodiment.
Figure 5:
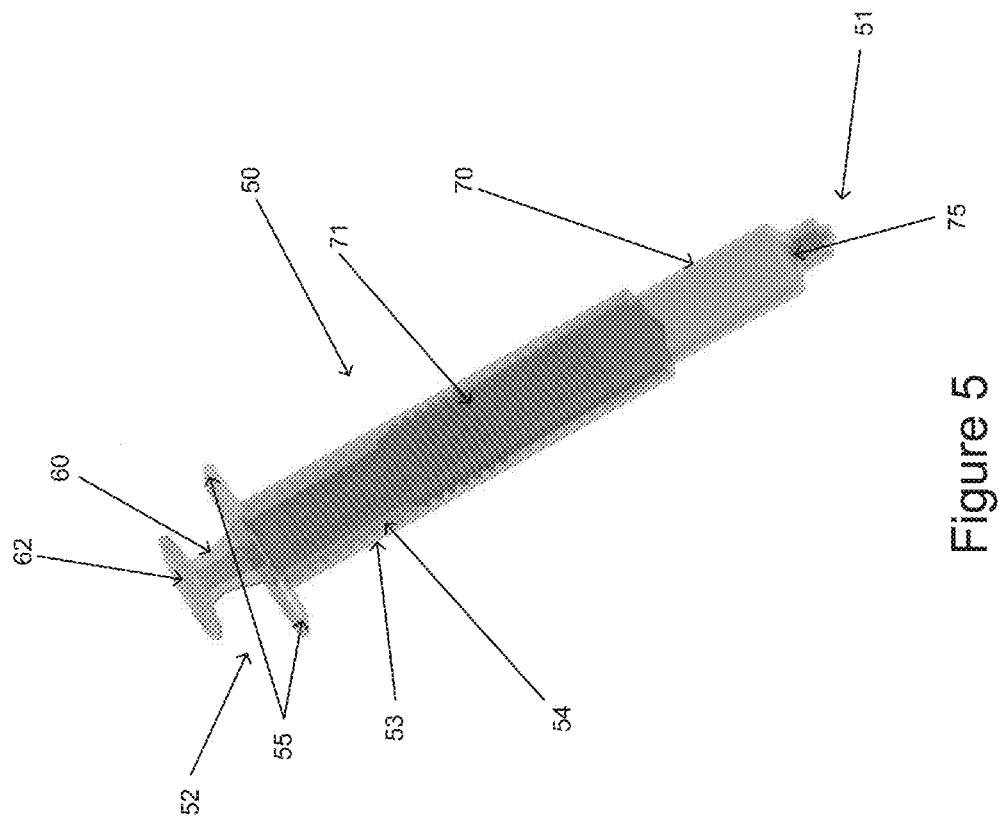
FIG. 5 is a perspective view of an example syringe according to another embodiment.
Figure 6:
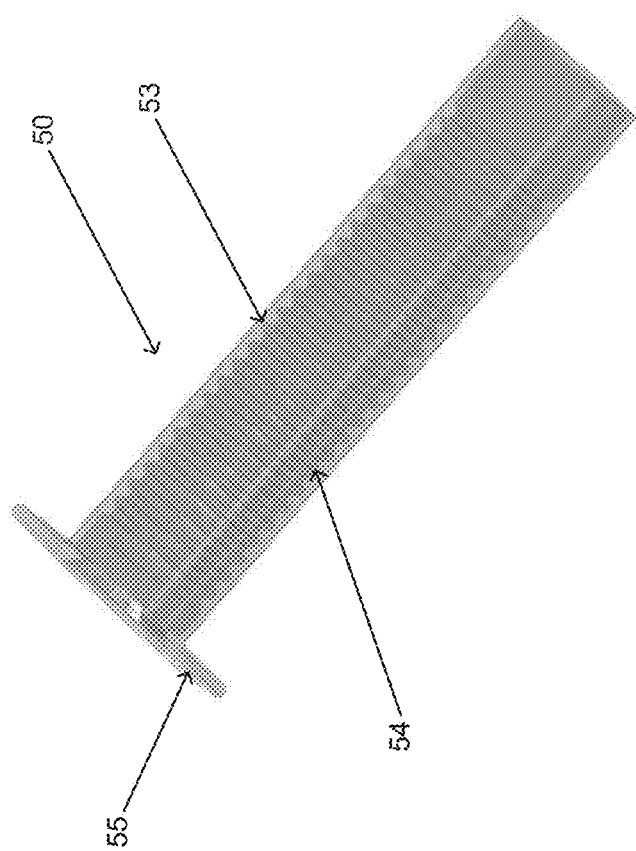
FIG. 6 is a perspective view of a dosage limiting sleeve of the syringe of FIG. 5.
Figure 7:
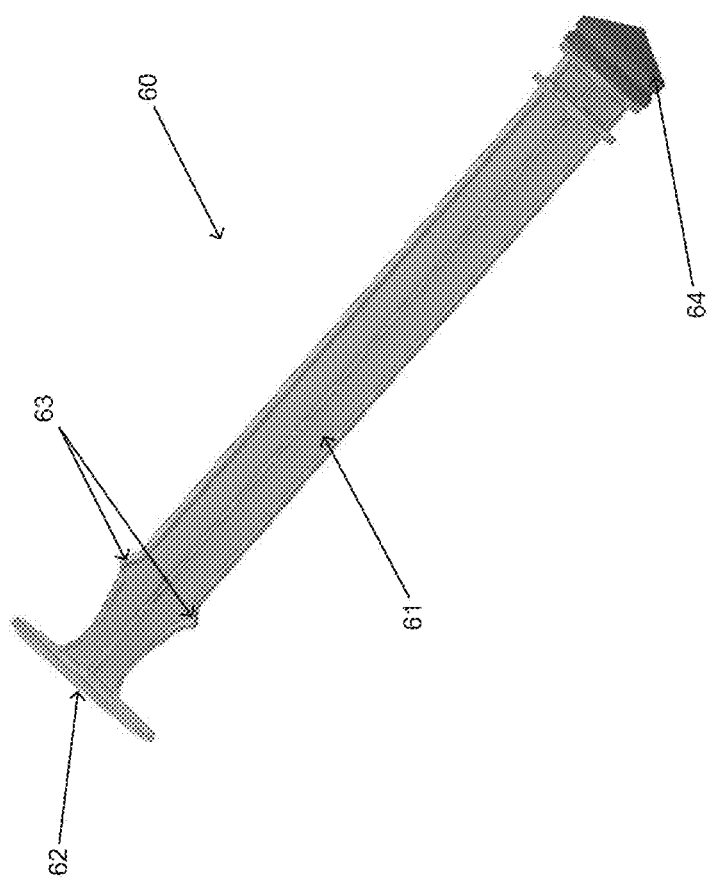
FIG. 7 is a perspective view of a plunger of the syringe of FIG. 5.
Figure 8:
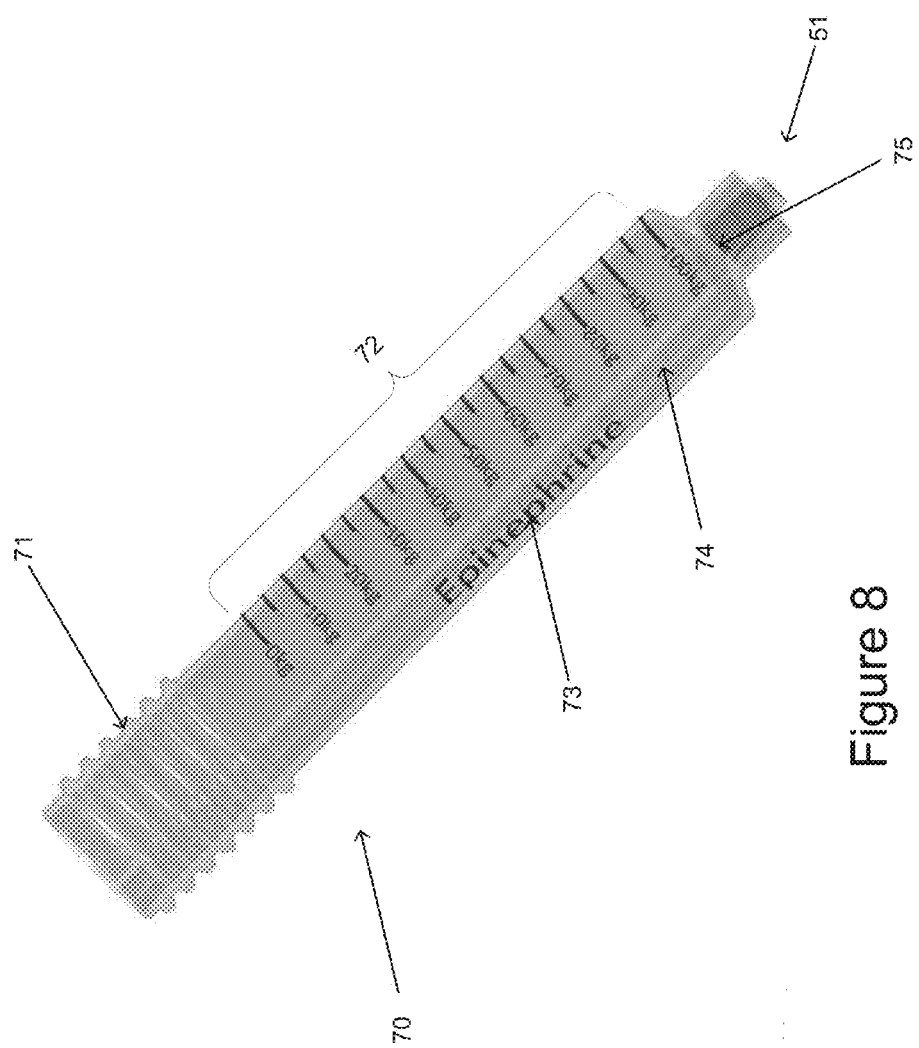
FIG. 8 is a perspective view of a syringe body of the syringe of FIG. 5.
Figure 9:
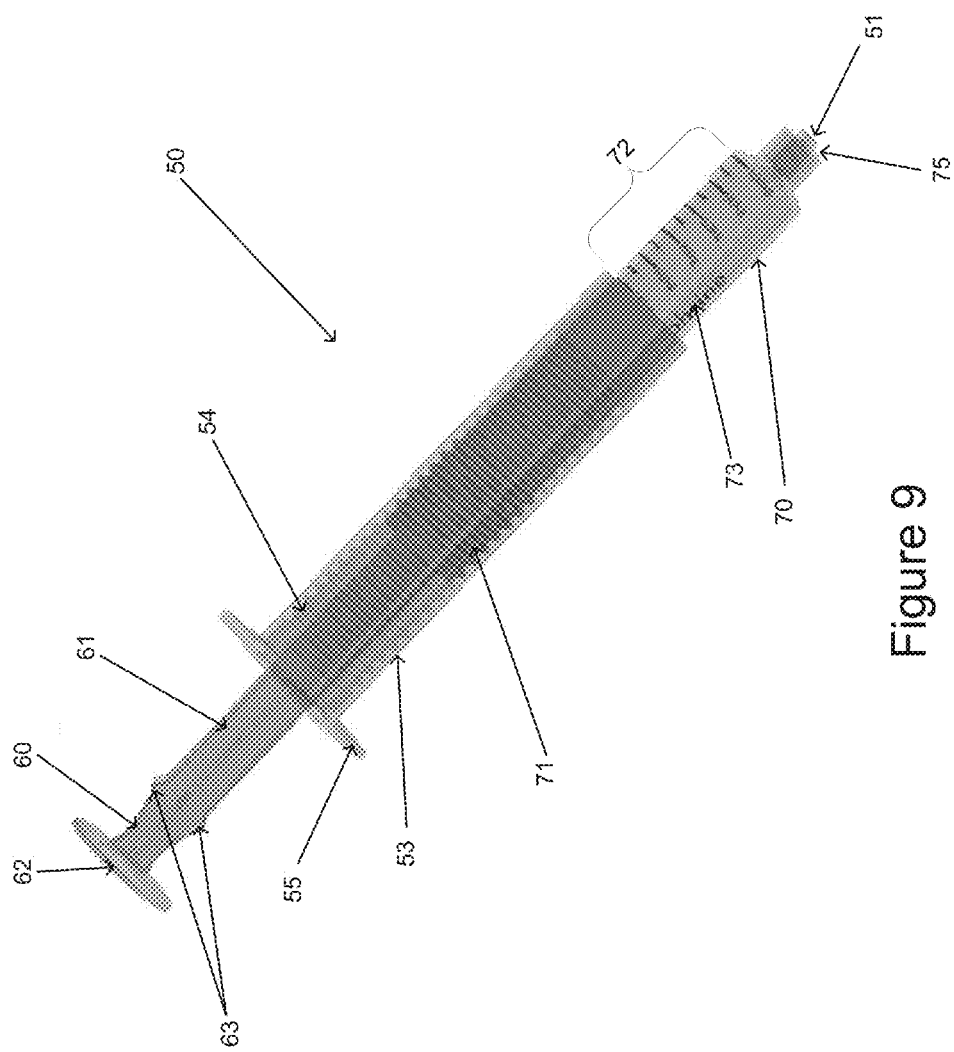
FIG. 9 is a perspective of view of the syringe of FIG. 5 in a dosed state.
Figure 10:
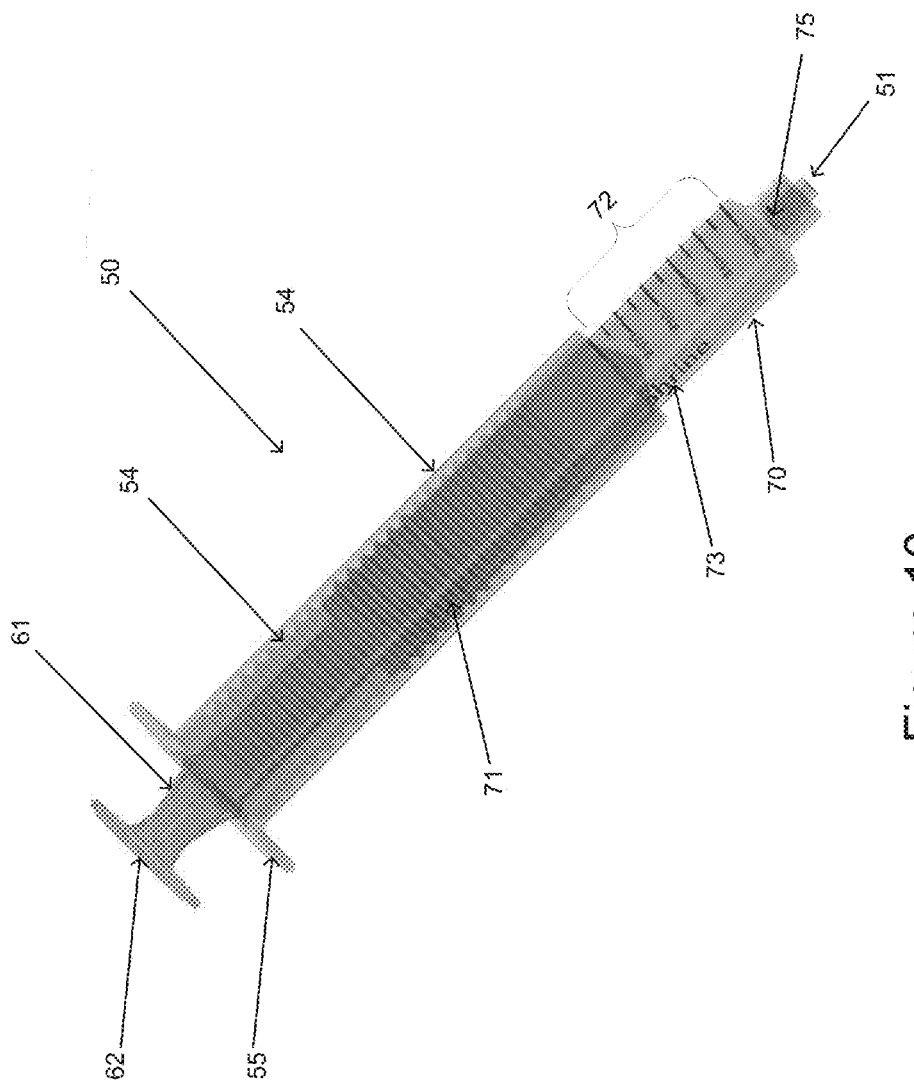
FIG. 10 is a perspective view of the syringe of FIG. 5 in a dispensed state.

The drawings are described in greater detail in the description and examples below.

DETAILED DESCRIPTION

The details of some example embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

The present disclosure relates in general to apparatuses and methods for increasing the safety of administration of a liquid medication, particularly under emergency conditions. Various embodiments described in the present disclosure provide drug delivery devices, such as syringes, and methods of enabling users to administer an appropriate dose of a medication from such devices while reducing the risk for error in determining and/or administering an appropriate dose of the medication, thus reducing the risk of patient harm.

Every health-care practitioner should expect to be involved in the treatment of medical emergencies during the course of clinical practice. Certain medical emergencies require the administration of an injectable medication for a favorable patient outcome. Under what may be very infrequently encountered conditions, a health-care practitioner may be required to assess a medical emergency, identify and access an appropriate medication, determine an appropriate amount to administer, and effectively administer a correct dosage, all while a patient is experiencing a life-threatening medical emergency. Under such conditions, mistakes can occur particularly as it is unlikely that a medical practitioner deals with such situations on a routine basis.

It has been recognized that certain steps may be taken to help mitigate risks involved in treatment of medical emergencies. For instance, the most commonly needed emergency medications are typically on hand and readily available at all medical treatment facilities, including but not limited to emergency rooms, operating rooms, clinics, emergency response vehicles, even dental care facilities.

Certain embodiments described in the present disclosure are designed to reduce or eliminate some of the potential sources of error faced by a user administering an injectable medication in a medical emergency.

In some embodiments an emergency injectable medication is provided pre-loaded in a syringe. These pre-loaded syringes may be color coded so as to indicate the category, if not the specific identity, of the medication contained therein. By way of example, pre-loaded syringes may be color coded according to conventional operating room protocols (i.e., purple for epinephrine, ephedrine, neosynephrine; green for atropine and glycopyrollate; blue for opioids; orange for benzodiazepenes; white for electrolyte solutions; etc.). However, it is to be understood that use of a color coding system does not typically replace traditional syringe labeling, e.g., labeling with the identity and concentration of the contents of the syringe. Further, use of a color coding system should not interfere with or prevent a user from viewing any identifying labeling that may be present on the pre-loaded syringe or prevent a user from measuring a dose for administration.

In some embodiments, syringes are provided that are labeled with non-volumetric graduations keyed to the identity and concentration of the contents of the pre-loaded syringe, such as graduations based on the weight of the patient. Such syringes have the advantage that a user is not required to recall the particular drug's dosage rate/kg, thus eliminating accurate recall of this detail as a potential source of error. Further, a user is not required to do a calculation to determine the appropriate volume of the keyed drug to administer. Instead, a user would merely select an amount to administer based on the weight of a patient. It should be noted that the use of non-volumetric graduations alone and/or in conjunction with various delivery systems/devices disclosed herein are not limited to syringe-needle assemblies for the injection of drugs into a patient, but may also include, e.g., needle-less systems/devices for the oral delivery of liquid medicines or formulas, or the delivery of a measured amount of liquid or other substance in any relevant context.

In some embodiments where the syringe is not pre-loaded (i.e., the user is required to draw an appropriate dose of a medication into the syringe prior to administration), the non-volumetric graduations may start at zero at the limit of plunger travel at the proximal end of the syringe (i.e., the end at which medication is dispensed) and go upwards to a maximum near the distal end of the syringe. Thus, a user would draw a dose for a particular patient into the syringe by drawing the syringe to the appropriate graduation for the particular patient. The entire volume then contained in the syringe would be the appropriate dose for the particular patient.

In some embodiments where the syringe is pre-loaded, non-volumetric graduations may start at zero at the pre-filled level near the distal end of the syringe and progress to a maximum at the limit of plunger travel at the proximal end of the syringe. In these embodiments, an appropriate dose for a particular patient is achieved by administering drug from the syringe until the proximal end of the plunger aligns with the graduation corresponding to the non-volumetric graduation appropriate for the particular patient.

In some embodiments, pre-loaded syringes are provided that comprise an adjustable means to limit plunger travel in a proximal direction, thus limiting the amount of drug that can be administered from the pre-loaded syringe to some amount less than the total amount of drug contained within the pre-loaded syringe. That is, pre-loaded syringes are provided that allow a user to limit the amount of medication administered from the syringe by preventing plunger travel in a proximal direction beyond a set distance. In some embodiments, plunger travel is limited in a proximal direction, but not in a distal direction.

An example pre-loaded syringe will be discussed with reference to FIGS. 1-4. An example embodiment 1 for storing and dispensing a liquid has a proximal end 2 and a distal end 3. The example embodiment comprises a syringe body 12 defining a void space 15 where a liquid is contained and dispensed therefrom. The syringe body 12 is attached to and at least partially surrounded by a housing 11. The housing 11 is attached to and disposed around the syringe body 12 in such a way so as to define a gap 13 between the housing 11 and the syringe body 12 that extends at least a portion of the length of the syringe body 12.

A dosage limiting sleeve 4 is adjustably disposed within gap 13 and contacts one or more of an outer surface of syringe body 12, an inner surface of housing 11, or both. The depth of the dosage limiting sleeve 4 within gap 13 serves to set the maximum distance a plunger 6 can travel in a proximal direction, thereby setting a maximum dosage to be administered. As the dose limiting sleeve is disposed in gap 13 between the housing 11 and the syringe body 12, the instant devices may be constructed such that no portion of the dose limiting sleeve 4 enters a void 15 defined by the syringe body 12.

Adjustability of the dosage limiting sleeve 4 may be accomplished by any suitable means as will be appreciated by one in the art. In some embodiments, an inner surface of the dosage limiting sleeve 4 and an outer surface of the syringe body 12 (i.e., a surface facing gap 13 and contacting an inner surface of dosage limiting sleeve 4) may be threaded so as to provide depth adjustment of the dosage limiting sleeve 4 within gap 13 by rotating the dosage limiting sleeve 4 relative to syringe body 12. Such an embodiment is seen in the cross-sectional view shown in FIG. 4, where threads 14 are seen disposed on an outer surface of the syringe body 12. The corresponding threads on the dosage limiting sleeve 4 are not shown.

Alternatively or in addition, an outer surface of the dosage limiting sleeve 4 and an inner surface of the housing 11 (i.e., a surface facing gap 13 and contacting an outer surface of dosage limiting sleeve 4) may be threaded so as to provide depth adjustment of dosage limiting sleeve 4 within gap 13 by rotating the dosage limiting sleeve relative to housing 11.

As seen in FIGS. 1-4, some portion of the dosage limiting sleeve 4 extends in a distal direction beyond the syringe body 12 and housing 11. This portion may comprise protuberances, wings, tabs, or other grip enhancing features (such as surface patterns) that facilitate adjustment of the depth of the dosage limiting sleeve 4 within gap 13. In the example embodiment shown in the Figures, the dosage limiting sleeve 4 is shown with optional tabs 5 for this purpose.

Housing 11 and syringe body 12 may be made of any suitable material so long as a portion of the housing 11 and syringe body 12 allow a user to view the liquid contained therein. In particular embodiments, housing 11 and syringe body 12 may comprise a clear, colorless material, such as an appropriate plastic, to allow a user to clearly view the contents of the syringe. The dosage limiting sleeve 4 may also be made of any suitable material, including a suitable plastic. Further, at least a portion of the dosage limiting sleeve 4 viewable by a user may be color coded to correspond with the category and/or identity of the specific medication contained within a syringe. One embodiment that includes this optional feature is seen in the Figures, in which the entire dosage limiting sleeve 4 is colored. However, in other embodiments, other color coding schemes may be employed, such as color coding only a portion of the dosage limiting sleeve 4, color coding all or a portion of a plunger (described below), etc. In fact, any portion of the device may be color coded so long as the color coding does not prevent a user from viewing any identifying labeling on the device, or prevent a user from metering a dose.

Also, as described above, the instant devices may be labeled with non-volumetric graduations, such as graduations based on the weight of the patient. This optional feature is seen as element 10 in the example embodiment shown in the Figures.

Additionally, the instant devices may be labeled with other information identifying the specific identity and concentration of the medication contained within. This optional feature is particularly relevant for pre-loaded syringe devices, and is seen as element 9 in the example embodiment shown in the Figures.

The instant devices also comprise a typical plunger 6 as previously known in the art. The plunger 6 comprises a piston rod 8 disposed at least partially within the syringe body 12. The plunger 6 further comprises a gasket 16 disposed at a proximal end of the piston rod 8 and a thumb pad 7 at a distal end of the piston rod 8. The gasket 16 is constructed of an appropriate material and is of an appropriate shape and size so as to form a seal by contacting the interior surface of the syringe body 12. In some embodiments, the gasket 16 and the piston rod 8 do not contact the dose limiting sleeve 4 at any point before, during, or after administration.

A plunger 6 also comprises a thumb pad 7, which in general is not intended to be limited in size and/or shape. However, in embodiments comprising a dose limiting sleeve 4, the thumb pad 7 has at least one dimension that exceeds an interior dimension of the dose limiting sleeve 4.

The operation of plunger 6 within a syringe body will be familiar to one of skill in the art, with the plunger 6 partially disposed within the syringe body 11 such that translational motion of the plunger 6 through the syringe body 11 in a proximal direction causes the contents of the syringe body to be ejected from the syringe body 11 at an opening 17.

In some embodiments, the lengths of the plunger 6 and the dosage limiting sleeve 4 are such that when the plunger 6 is fully depressed and a proximal surface of the thumb pad 7 is in contact with the distal end of the dosage limiting sleeve 4, a proximal end of the plunger 6 aligns with a proximal end of the dosage limiting sleeve 4.

In some embodiments, devices described herein may further comprise a hypodermic needle of appropriate length and diameter for an intended injectable medication. In some embodiments, a device may be constructed with a hypodermic needle integral to and/or permanently affixed to a proximal end 2 of the device. Alternatively, the device may be constructed such that a proximal end 2 may be configured to releasable receive a hypodermic needle by any suitable means known in the art, such as screw threading or a Luer lock.

Thus, the example pre-loaded syringe shown in FIGS. 1-4 may be used as follows. A user assesses or obtains the weight of a patient in need of administration of an injectable medication contained within the example pre-loaded syringe device. The user adjusts the depth of the dosage limiting sleeve 4 so that a proximal end of the sleeve 4 aligns with a graduation indicating a desired dose. Using the particular embodiment shown in the Figures, this means that a user adjusts the depth of the dosage limiter sleeve 4 so that the proximal end of sleeve 4 aligns with an appropriate weight graduation 10 corresponding to the weight of the patient. The user administers the liquid contained in the syringe by depressing the thumb pad 7, thereby moving the plunger 6 in a proximal direction and expelling the liquid through opening 17, until a proximal surface of the thumb pad 7 contacts a distal end of the dose limiting sleeve 4. Once the thumb pad 7 contacts a distal end of the dosage limiting sleeve 4, the desired dose has been delivered and plunger 6 is prevented from further travel.

An example syringe configured in accordance with another embodiment will be discussed with reference to FIGS. 5-10. Similar to the example pre-loaded syringe illustrated in FIGS. 1-4, the example syringe of FIGS. 5-10 may be pre-loaded with an emergency injectable medication. Syringe 50 for storing and dispensing a substance, such as a liquid medication, may have a proximal end 51, and a distal end 52. Example syringe 50 may include a syringe body 70 that can define a void space 74 from which a substance can be drawn into and/or contained and dispensed.

Syringe 50 may further include a dosage limiting sleeve 53 that is adjustably attached or secured over or about syringe body 70. In this embodiment, unlike the example pre-loaded syringe of FIGS. 1-4, a separate housing, dosage limiting sleeve, and syringe body are not required, as syringe body 70 and dosage limiting sleeve 53 operate in conjunction with or directly contact each other as will be described in greater detail below. The depth which syringe body 70 is set within dosage limiting sleeve 53 can serve to set the maximum distance a plunger 60 can travel in a proximal direction, thereby setting a maximum dosage to be administered.

Adjustability of dosage limiting sleeve 53 may be accomplished by any suitable mechanism(s) as will be appreciated by one in the art. In some embodiments, an inner surface of the dosage limiting sleeve 53 and an outer/exterior surface of syringe body 70 may be cooperatively threaded so as to provide depth adjustment of dosage limiting sleeve 53. Such depth adjustment may be achieved by rotating dosage limiting sleeve 53 relative syringe body 70, by rotating syringe body 70 relative to dosage limiting sleeve 53, or alternatively still by, e.g., simultaneously rotating both syringe body 70 and dosage limiting sleeve 53 in opposite directions relative to each other. For example, dosage limiting sleeve 53 may have female or internal threads 54 disposed on an inner surface of dosage limiting sleeve 53, and syringe body 70 may have corresponding male or external threads 71 disposed on its exterior surface. It should be noted that frictional force(s) via the corresponding threading can maintain the positions of dosage limiting sleeve 53 and syringe body 70 relative to each other.

However, other methods of adjustably connecting dosage limiting sleeve 53 and syringe body 70 may be utilized in accordance with other embodiments. For example, a rack and pinion mechanism may be employed, where one of dosage limiting sleeve 53 and syringe body 70 can be embodied as the "rack" along which the pinion can travel, an alternative one of syringe body 70 and limiting sleeve 53 having integrated therein, the "pinion." Alternatively still, instead of a rack and pinion mechanism, two sets of linear teeth or gearing configured to engage with each other can be disposed on an inner surface of dosage limiting sleeve 53 and on an exterior surface of syringe body 70. Moreover, although not necessary, some form of locking or semi-lockable mechanism may also be utilized in various embodiments to secure the relative positioning of dosage limiting sleeve 53 and syringe body 70.

Dosage limiting sleeve 53 may extend in a distal direction beyond syringe body 70. Accordingly, a portion of dosage limiting sleeve 53 that extends beyond syringe body 70 may include protuberances, wings, tabs, or other grip enhancing features (such as surface patterns) that can facilitate adjustment of the depth of dosage limiting sleeve 53 and/or provide additional surface area that a user may utilize to assist with the dispensing of the liquid medication contained in syringe body 70 (in particular, void space 74). To that end, syringe 50 may comprise tabs 55.

Syringe body 70 may be made of any suitable material so long as at least a portion of syringe body 70 allows a user to view any substance(s) contained therein. In some embodiments, syringe body 70 may be manufactured from or made of a clear, colorless material, including, but not limited to an appropriate plastic, to allow a user to clearly view the contents of syringe 50. Dosage limiting sleeve 53 may also be made of any suitable material, including but not limited to a suitable plastic, and can also allow for viewing of the contents of syringe 50. Further, at least a portion of the dosage limiting sleeve 53 viewable by a user may be color coded to correspond with the category and/or identity of the specific substance(s) contained within syringe 50. However, in other embodiments, other color coding schemes may be employed, such as color coding only a portion of dosage limiting sleeve 53, color coding all or a portion of plunger 60 (described below), etc. In fact, any portion of syringe 50 may be color coded so long as the color coding does not prevent a user from viewing any identifying labeling on the device, or prevent a user from metering a dose.

Also, as described above, syringe 50 may be labeled with non-volumetric graduations, such as graduations 72 which are based on the weight of the patient rather than a volumetric amount or value associated with the substance(s) contained in or to be dispensed from syringe 50. It should be noted that non-volumetric graduations and/or concentrations may be displayed using other units of measure, such as pounds, for example, instead of kilograms. It should further be noted that the density of the threading disposed on syringe body 70 and dosage limiting sleeve 53 can be varied in accordance with different embodiments to achieve differing sensitivity and/or accuracy of dosing. For example, a syringe with greater thread density or finer threads may result in the ability to fine-tune, e.g., the non-volumetric dosage (which may be more suited to a non-emergency pediatric context), than a syringe with lesser thread density or coarser/larger-gapped threads (which may be suitable in an adult emergency context).

Additionally, syringe 50 may be labeled with other information identifying the specific identity and/or concentration of the substance(s) contained within syringe 50. As previously indicated, such a feature may be particularly relevant for pre-loaded syringe devices, and is seen as element 73 on syringe 50.

Syringe 50 may also include a plunger 60. Plunger 60 may comprise a piston rod 61 that can be disposed at least partially within syringe body 70, a gasket 64 disposed at a proximal end of piston rod 61, and a thumb pad 62 at a distal end of the piston rod 8. Gasket 64 can be constructed of an appropriate material and is of an appropriate shape and size so as to form a seal by contacting an interior surface of syringe body 70 for drawing into and dispensing a substance from void space 74 of syringe body 70 through opening 75. Plunger 60 may further comprise one or more stop tabs 63 configured to prevent plunger 60 from being disposed past or beyond a distal end of dosage limiting sleeve 53 (e.g., substantially at tabs 55 in one embodiment).

Operation of plunger 60 within syringe body 70 will be familiar to one of skill in the art. That is, and for dispensing purposes, plunger 60 can be at least partially disposed within syringe body 70 such that translational motion of plunger 60 through and along at least a portion of the longitudinal length of syringe body 70 in a proximal direction causes the contents of syringe body 70 to be ejected from syringe body 70 at opening 75.

In some embodiments, the lengths of plunger 60 and dosage limiting sleeve 53 are such that when plunger 60 is fully depressed, a proximal surface of thumb pad 62 does not come into contact with a distal end of dosage limiting sleeve 53 by virtue of stop tabs 63 contacting the distal end of dosage limiting sleeve 53 (e.g., approximately at tabs 55), and a proximal end of plunger 60 substantially aligns with a proximal end of dosage limiting sleeve 53.

In some embodiments, syringe 50 may further comprise a hypodermic needle of appropriate length and diameter for an intended injectable medication (not shown). In some embodiments, a device may be constructed with a hypodermic needle integral to and/or permanently affixed to a proximal end 51 of syringe 50. Alternatively, syringe 50 may be constructed such that proximal end 51 may be configured to releasably receive a hypodermic needle by any suitable means known in the art, such as screw threading or a Luer lock.

Thus, syringe 50 may be operated as follows. A user can assess or obtain the weight of a patient in need of administration of an injectable medication contained within syringe 50. The user can adjust the depth of syringe body 70 within dosage limiting sleeve 53 so that a proximal end of the sleeve 4 aligns with a graduation indicating a desired dose. Using the particular embodiment shown in the Figures, this means that a user adjusts the depth of the dosage limiter sleeve 4 such that the proximal end of dosage limiting sleeve 53 substantially aligns with an appropriate non-volumetric (e.g., weight) graduation 72 corresponding to the weight of the patient. The user administers the liquid contained in syringe 50 by depressing thumb pad 62, thereby moving plunger 60 in a proximal direction towards proximal end 51 of syringe 50 and expelling the liquid through opening 75, until stop tabs 63 contact a distal end of dosage limiting sleeve 53. Once stop tabs 63 contact the distal end of the dosage limiting sleeve 53, the desired dose has been delivered and plunger 60 is prevented from further travel in the proximal direction.

As described above, in some embodiments, syringes are provided that are labeled with non-volumetric graduations keyed to the identity and concentration of the contents of the pre-loaded syringe, such as graduations based on the weight of the patient in order to alleviate the pressure on a user to make accurate/correct conversion calculations to account for a patient's weight. Therefore, and to provide the same or similar functionality with volumetric labeled or non-labeled syringe devices, a sticker or other adhesive material having non-volumetric graduations is provided in accordance with still another embodiment.

Figure 11:
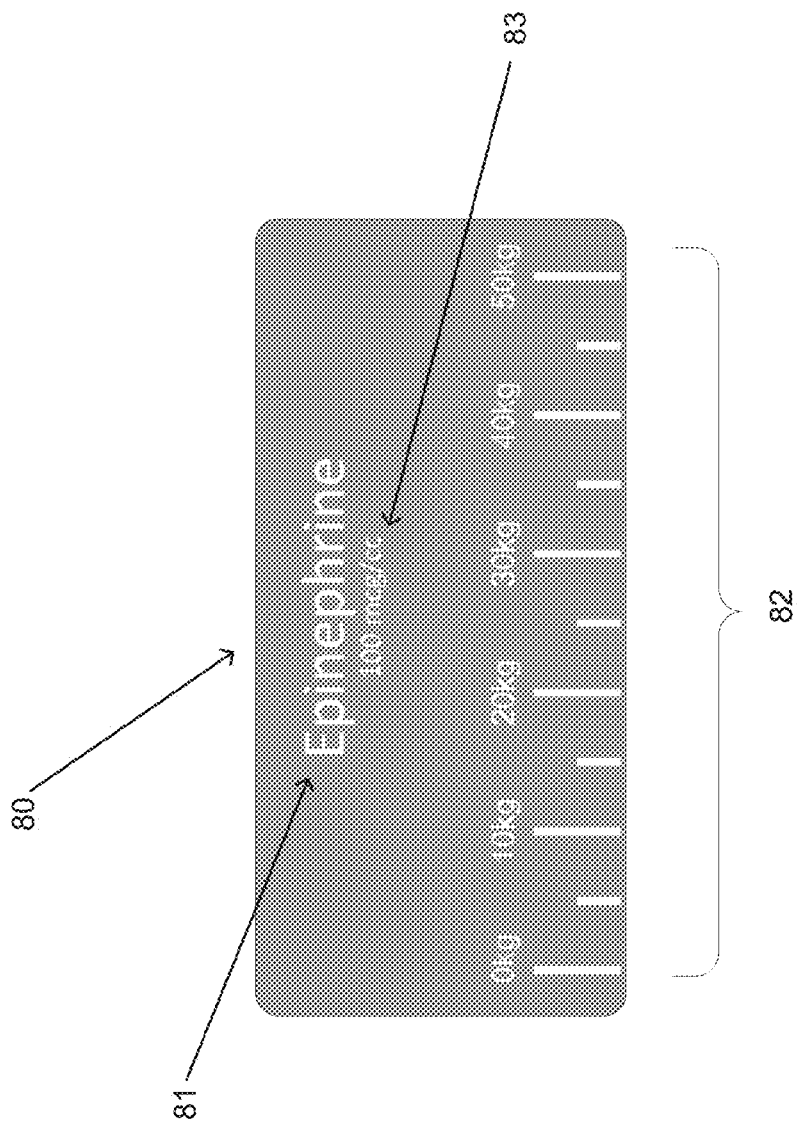
FIG. 11 illustrates an example non-volumetric graduated sticker in accordance with one embodiment.

FIG. 11 illustrates an example sticker 80 having non-volumetric graduations 82 displayed thereon. Additionally, the identity of the substance(s)/medication contained in a syringe device may be indicated by element 81, along with an indication of concentration indicated by element 83. More/additional or less indications may be displayed on sticker 80 in accordance with various embodiments, and other.

It should be noted that sticker 80 may be any appropriate adhesive or attachable material capable of displaying non-volumetric graduations, such as a decal, label, or other transfer made of plastic, paper, or other substrate. In one embodiment, non-volumetric graduations 82 may be disposed on a first surface of sticker 80, while a second surface of sticker 80 may contain an adhesive material or substance. In another embodiment, non-volumetric graduations 82 may be disposed on the same side as the adhesive surface, wherein sticker 80 may be manufactured from a clear or transparent material allowing non-volumetric graduations 82 to be seen through the non-adhesive surface. Additionally, non-volumetric graduations and/or concentrations may be displayed using other units of measure, such as pounds, for example, instead of kilograms, mcg/ml instead of mcg/cc, etc. In accordance with various embodiments, sticker 80 may be substantially clear or translucent, and one or more portions of sticker 80 or the entirety of sticker 80 may be color coded as described above. Sticker 80 may be used by applying sticker 80 to, e.g., a non-labeled syringe device. In the case of an already-labeled syringe device, sticker 80 may be applied to an area of the already-labeled syringe device that is devoid of labeling, or if translucent, may be applied over existing labeling to substantially cover up the existing labeling, while allowing the non-volumetric graduations to still be visible to a user.

As will be appreciated by those of skill in the art, use of syringe devices in accordance with various embodiments are not intended to be limited to any particular medication. Rather, any appropriate medication may be stored in and/or dispensed from the instant devices, so long as the medication may be stored in and/or dispensed from a syringe type device. In various embodiments, a medication may be selected from the group consisting of an inotrope (such as epinephrine, ephedrine, neosynephrine, etc.), an anticonvulsant, an analgesic, a vasopressor, an antihypoglycemic, a corticosteroid, an antihypertensive, an anticholinergic, an antiarrhythmic, a vasodilator, and an antidotal.

It is also not intended that syringe devices in accordance with various embodiments are limited with respect to volumetric capacity and/or non-volumetric amounts. Syringe devices in accordance with various embodiments may be constructed to hold any necessary amount of an intended medication. Additionally, although the example syringe devices shown in the Figures comprise substantially concentric cylindrical housings and/or syringe bodies and, the cross-sectional shapes of the syringe body and/or housing are not necessarily limited as such. Any desired cross-sectional shape of the syringe body, housing, or both may be used.

Further still, the use of non-volumetric graduations alone and/or in conjunction with various delivery systems/devices disclosed herein are not limited to syringe-needle assemblies for the injection of drugs into a patient, but may also include, e.g., needle-less systems/devices for the oral delivery of liquid medicines or formulas, or the delivery of a measured amount of liquid or other substance in any relevant context.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

Various embodiments of the present disclosure have been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

What is claimed is:

1. A syringe comprising:
   a syringe body for storing and dispensing a substance contained within the syringe body;
   a plunger arranged partially within the syringe body such that translational motion of the plunger in a proximal direction causes the substance to be dispensed from the syringe body; and
   a dosage limiting sleeve coupled to an exterior surface of the syringe body and extending in a distal direction beyond a distal end of the syringe body, wherein a distal end of the dosage limiting sleeve is configured to interact with the plunger so as to prevent the translational motion of the plunger in the proximal direction beyond a predetermined point, and wherein the dosage limiting sleeve does not limit translational motion of the plunger in a distal direction as an interior surface of the dosage limiting sleeve comprises a first plurality of threads and the exterior surface of the syringe body comprises a second plurality of threads to be engaged with the first plurality of threads to provide depth adjustment of the dosage limiting sleeve and to couple the syringe body with the dosage limiting sleeve, wherein the syringe body or the dosage limiting sleeve comprises non-volumetric graduations keyed to an identity and concentration of the substance such that the graduations indicate an appropriate dosage of the substance by patient weight.

2. The syringe of claim 1, wherein the syringe body is colorless and transparent.

3. The syringe of claim 1, wherein the dosage limiting sleeve is made of a colored material.

4. The syringe of claim 1, wherein a color of the dosage limiting sleeve is an indication as to a category or identity of the substance contained in the syringe body.

5. The syringe of claim 1, wherein a portion of the dosage limiting sleeve that extends beyond the distal end of the syringe body further comprises one or more outwardly directed protuberances, wings, tabs, or other surface modifications for enhancing at least one of grip and rotational actuation of at least one of the syringe body and the dosage limiting sleeve.

6. The syringe of claim 1, wherein the engagement of the first and second plurality of threads provides for rotational adjustment of the syringe body and the dosage limiting sleeve relative to each other.

7. The syringe of claim 6, wherein the engagement of the first and second plurality of threads provides for metering a desired amount of the substance to be dispensed from the syringe body.

8. The syringe of claim 7, wherein the plunger further comprises at least one tab configured to dispense the desired amount of the substance by preventing the translational motion of the plunger in the proximal direction beyond the distal end of the dosage limiting sleeve.

* * * * *